(12) United States Patent
Molettiere et al.

(10) Patent No.: US 9,048,923 B2
(45) Date of Patent: Jun. 2, 2015

(54) SYSTEM AND METHOD FOR WIRELESS DEVICE PAIRING

(71) Applicant: Fitbit, Inc., San Francisco, CA (US)

(72) Inventors: Peter Andrew Molettiere, San Francisco, CA (US); James Park, Berkeley, CA (US); Aislinn Abigail Bilodeaux-Dewey, San Francisco, CA (US); Christine Boomer Brumback, San Francisco, CA (US); Eric Nathan Friedman, San Francisco, CA (US); Robert Curtis Cole, Los Altos, CA (US); Heiko Gernot Albert Panther, Oakland, CA (US); Andrew Cole Axley, Oakland, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/140,208

(22) Filed: Dec. 24, 2013

(65) Prior Publication Data

US 2014/0235168 A1  Aug. 21, 2014

Related U.S. Application Data

(62) Division of application No. 13/769,350, filed on Feb. 17, 2013.

(51) Int. Cl.
| | |
|---|---|
| *H04B 7/00* | (2006.01) |
| *H04B 7/26* | (2006.01) |
| *A61B 5/00* | (2006.01) |
| *H04W 4/00* | (2009.01) |
| *H04W 76/02* | (2009.01) |
| *H04W 8/00* | (2009.01) |
| *G06F 19/00* | (2011.01) |

(52) U.S. Cl.
CPC ............... *H04B 7/26* (2013.01); *H04W 8/005* (2013.01); *A61B 5/0004* (2013.01); *A61B 5/0022* (2013.01); *H04W 4/008* (2013.01); *H04W 76/023* (2013.01); *G06F 19/30* (2013.01)

(58) Field of Classification Search
None
See application file for complete search history.

(56) References Cited

U.S. PATENT DOCUMENTS

| | | | |
|---|---|---|---|
| 6,772,331 B1 * | 8/2004 | Hind et al. | 713/151 |
| 6,845,097 B2 * | 1/2005 | Haller et al. | 370/352 |
| 7,865,140 B2 | 1/2011 | Levien et al. | |
| 7,907,901 B1 | 3/2011 | Kahn et al. | |
| 7,925,022 B2 | 4/2011 | Jung et al. | |
| 7,941,665 B2 | 5/2011 | Berkema et al. | |
| 8,059,573 B2 | 11/2011 | Julian et al. | |
| 8,095,071 B2 | 1/2012 | Sim et al. | |
| 8,103,247 B2 | 1/2012 | Ananthanarayanan et al. | |
| 8,190,651 B2 | 5/2012 | Treu et al. | |
| 8,213,613 B2 | 7/2012 | Diehl et al. | |
| 8,260,261 B2 | 9/2012 | Teague | |

(Continued)

*Primary Examiner* — Zhiyu Lu
(74) *Attorney, Agent, or Firm* — Courtney IP Law; Barbara B. Courtney

(57) ABSTRACT

Embodiments of the present invention include a system and method for wirelessly identifying and validating an electronic device in order to initiate a communication process with another device or a service. In an embodiment, the system includes a portable biometric monitoring device that is identified by a client device or a server for the purpose of initiating a pairing process. In an embodiment, pairing implies pairing the portable device to an online user account with minimal user interaction. After pairing, the portable device and appropriate client devices and servers communicate with little or no user interaction, for example to upload sensor data collected by the portable device.

13 Claims, 14 Drawing Sheets

(56) References Cited

U.S. PATENT DOCUMENTS

| | | |
|---|---|---|
| 8,271,662 B1 | 9/2012 | Gossweiler, III et al. |
| 2004/0192383 A1* | 9/2004 | Zacks et al. .................. 455/557 |
| 2005/0245793 A1* | 11/2005 | Hilton et al. .................. 600/300 |
| 2006/0195695 A1* | 8/2006 | Keys ............................. 713/169 |
| 2006/0234631 A1* | 10/2006 | Dieguez ........................ 455/41.2 |
| 2006/0281409 A1* | 12/2006 | Levien et al. ................. 455/41.2 |
| 2007/0186105 A1* | 8/2007 | Bailey et al. .................. 713/168 |
| 2008/0200774 A1* | 8/2008 | Luo ................................ 600/301 |
| 2010/0043056 A1 | 2/2010 | Ganapathy |
| 2010/0052870 A1* | 3/2010 | King ......................... 340/286.02 |
| 2010/0058064 A1* | 3/2010 | Kirovski et al. .............. 713/176 |
| 2010/0210287 A1* | 8/2010 | De Vries et al. ............ 455/456.3 |
| 2010/0222000 A1* | 9/2010 | Sauer et al. ................... 455/41.2 |
| 2010/0245585 A1* | 9/2010 | Fisher et al. .................. 348/164 |
| 2011/0223862 A1* | 9/2011 | Satoh et al. ................... 455/41.2 |
| 2011/0258689 A1* | 10/2011 | Cohen et al. ....................... 726/7 |
| 2012/0221634 A1 | 8/2012 | Treu et al. |
| 2012/0254987 A1 | 10/2012 | Ge et al. |
| 2012/0289159 A1* | 11/2012 | Palin et al. .................... 455/41.2 |
| 2012/0297229 A1 | 11/2012 | Desai et al. |
| 2012/0297440 A1 | 11/2012 | Reams et al. |
| 2013/0080113 A1* | 3/2013 | Yuen et al. .................... 702/160 |
| 2013/0189925 A1* | 7/2013 | Staskawicz et al. ......... 455/41.1 |
| 2014/0068713 A1* | 3/2014 | Nicholson et al. ................ 726/3 |

\* cited by examiner

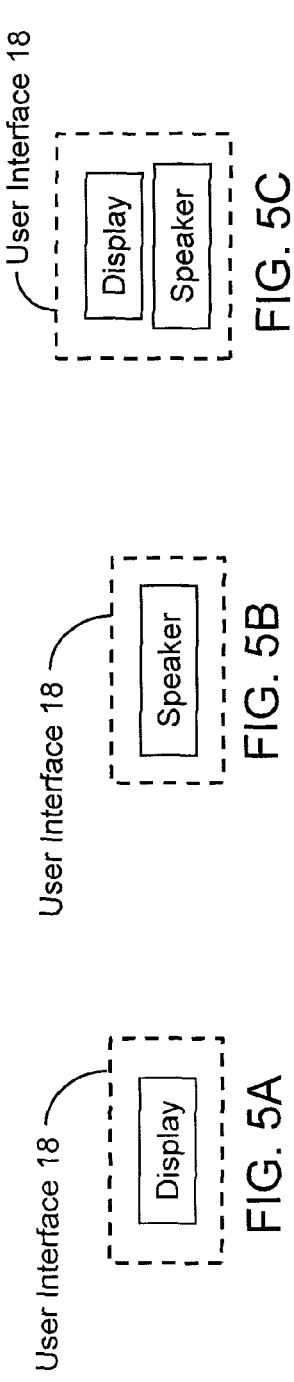
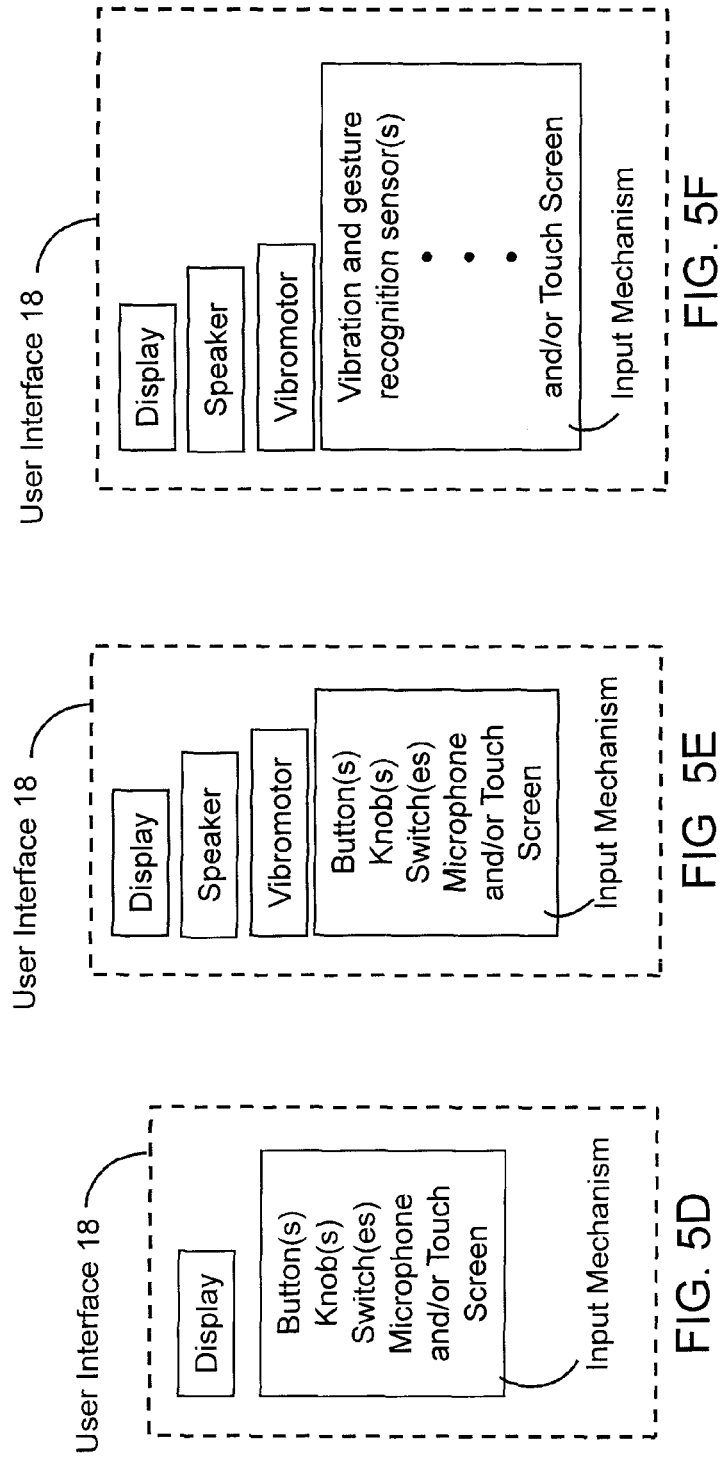
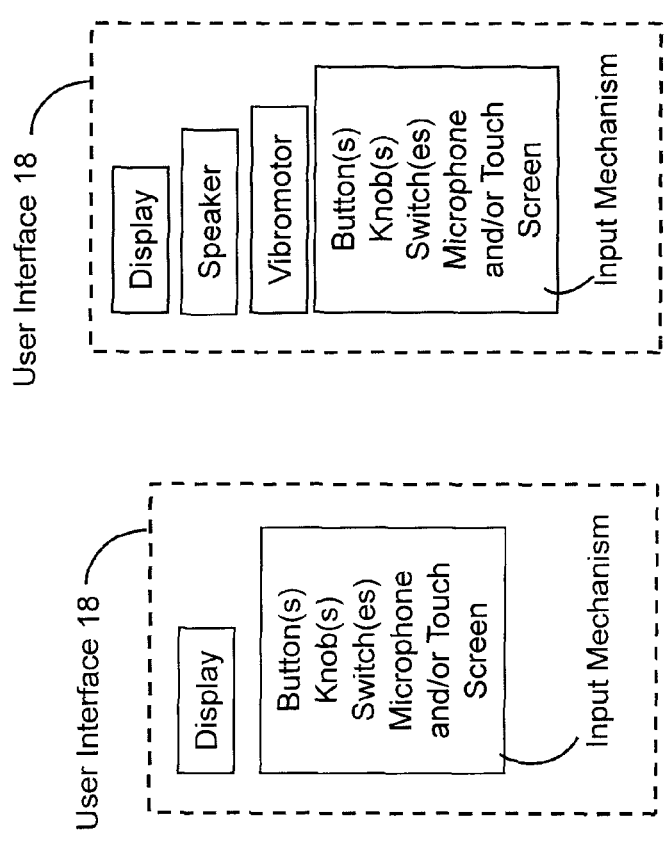
FIG. 5A FIG. 5B FIG. 5C FIG. 5D FIG. 5E FIG. 5F

SYSTEM AND METHOD FOR WIRELESS DEVICE PAIRING

RELATED APPLICATIONS

This application is a division of U.S. patent application Ser. No. 13/769,350, filed Feb. 17, 2013, and titled system and method for wireless device pairing, which is incorporated by reference in its entirety herein. U.S. patent application Ser. No. 13/769,350 is related to U.S. patent application Ser. No. 13/156,304, filed Jun. 8, 2011, and titled PORTABLE MONITORING DEVICES AND METHODS OF OPERATING SAME which is incorporated by reference herein in its entirety. U.S. patent application Ser. No. 13/769,350 is further related to U.S. patent application Ser. No. 13/674,265, also titled PORTABLE MONITORING DEVICES AND METHODS OF OPERATING SAME, filed Nov. 11, 2012 which is a division of U.S. patent application Ser. No. 13/156,304, and which is also incorporated by reference herein in its entirety.

BACKGROUND

The use of wired and wireless portable electronic devices continues to grow. Individuals typically own and use multiple portable devices, each of which has one or more particular functions, including cell phones, personal digital assistants, navigation devices, and body monitoring or fitness-oriented devices. These devices are often used in addition to non-portable devices such as desktop computers. It is expected that these various devices can communicate with the Internet and/or with each other for uploading and downloading data or otherwise transferring data. One example of a portable device that communicates with the internet and other devices is a monitoring device that is intended to be small and easily worn on or about the body. When monitored data is collected by the device, it is desirable to transfer the data (sometimes after on-board processing and sometimes before on-board processing) to other devices so that the user can easily review the data or possibly operate on it. In order for a portable device to communicate with another device or for it to be associated with a user specific account, the device is usually initially paired to an online account and/or to another device. Typically, this involves authentication, and also identification or verification of the device to be paired. Authentication includes verifying that the user is authorized to access the account to which data will be uploaded from the device, or from which data will be transmitted. Identification of the device can include discovery of the device by client software (such as software on a personal computer (PC) in communication with a cloud-based server) that is programmed to look for specific identifying information. It is desirable to minimize the amount of user interaction and input required in the pairing process for ease of use. This is particularly true of small devices which are purposely designed to eliminate keyboards and multiple buttons in order to satisfy other design criteria.

BRIEF DESCRIPTION OF THE DRAWINGS

FIGS. 5A-5F are block diagrams of user interfaces according to various embodiments.

DETAILED DESCRIPTION

Figure 1:
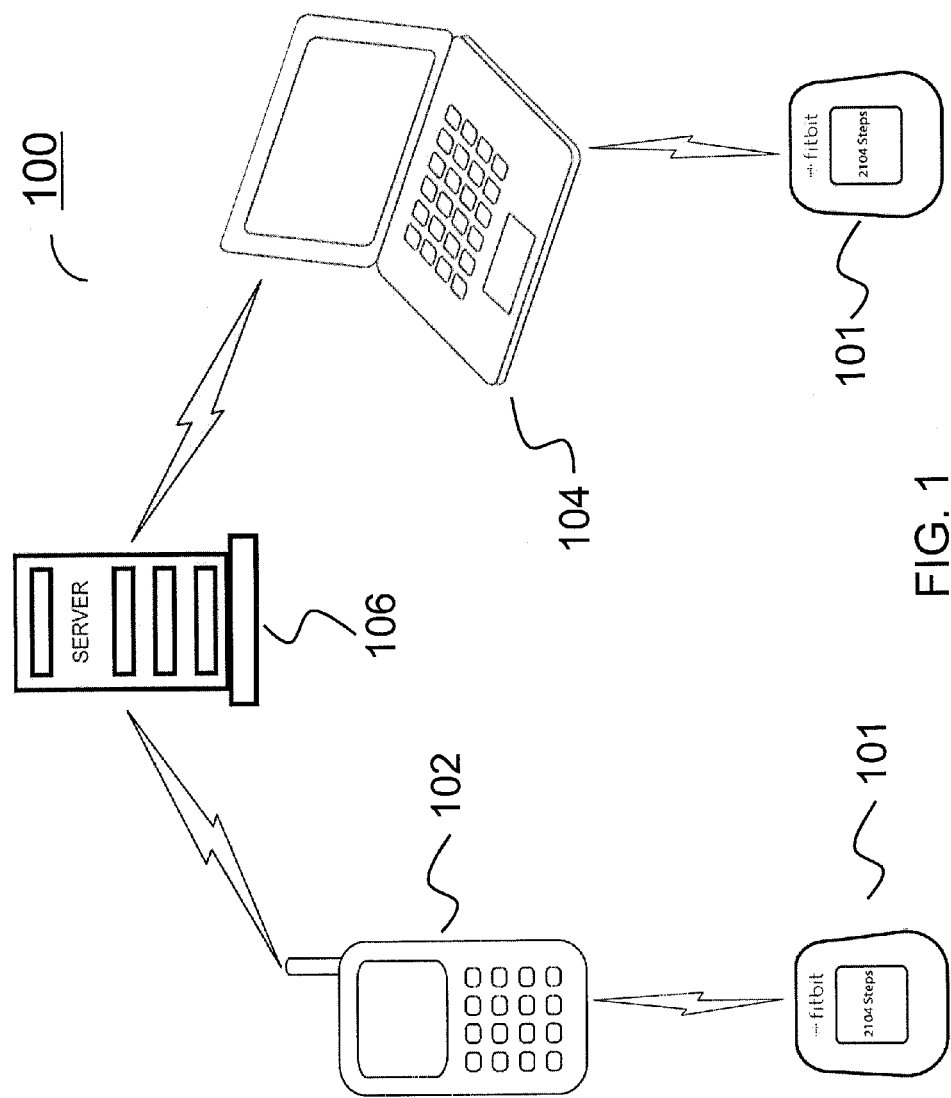
FIGS. 1-4 are block diagrams of portable device systems according to various embodiments.

Embodiments of the present invention include a system and method for wirelessly identifying and validating an electronic device in order to initiate a communication process with another device or a service. In an embodiment, the system includes a portable biometric monitoring device that is identified by a client device or a server for the purpose of initiating a pairing process. In an embodiment, pairing implies pairing the portable device to an online user account with minimal user interaction. After pairing, the portable device and appropriate client devices and servers communicate with little or no user interaction, for example to upload sensor data collected by the portable device. In one embodiment, the portable device is detected or discovered by a client or by a server when the device is in close enough proximity. The client or server causes the portable device to indicate to the user that the client or server wants to initiate a pairing process. For example, the portable device vibrates to indicate that the client or server is requesting to pair. In an embodiment, the user taps the device on any part of its surface to initiate the pairing process. Tapping includes touching the device on any part of its exterior. No particular location or button needs to be touched for the user to make the user input. Tapping includes light touching once or multiple times. No additional user input is required to complete the pairing process. After pairing, the portable device is associated with a user account that stores data collected by the portable device (data exclusive to the user). The account also stores any personal information the user chooses to enter (for example via a web site). After pairing using a particular client (for example a cell phone), the client wirelessly communicates with the portable device, but not with other, similar portable devices that were not paired. A Fitbit™ portable biometric monitoring device is used as an example of a device in this disclosure, but the invention is not so limited. After the device is paired though a user's cell phone to a user account, the cell phone will communicate with the device, and also with any server in proximity, to exchange data. However, the cell phone will not recognize the Fitbit™ devices of other users. In addition, the Fitbit™ device of one user cannot access or communicate with the Fitbit™ account of another user.

Pairing can include linking devices in order to send information between devices. Pairing also includes pairing between a device and a service. In a client-server embodiment, the method is used to pair a device with an account resident on a server through a client. In another embodiment, the method is used to pair a device directly to a server. A portable biometric device is used as an example of a portable device that can be paired according to the invention disclosed herein. However, the invention is not limited to a portable biometric device. Throughout this disclosure by way of example, reference is made to a portable biometric monitoring device, aspects of which are described and claimed in copending U.S. patent application Ser. No. 13/156,304, filed Jun. 8, 2011, which is incorporated by reference in its entirety herein.

Devices which are not considered portable biometric devices, but may be paired according to the invention disclosed herein include, but are not limited to portable or non-portable devices such as weight scales, body fat scales, exercise equipment, blood glucose meters, pulse oximeters, blood pressure cuffs, and, in one embodiment mobile phones. The term "weight scale" is used to refer to a device having a platform capable of supporting the weight of a user. In an embodiment, a weight scale contains multiple sensors including, but not limited to Body Impedance or biomolecular-interaction analysis (BIA) sensors to measure body fat, weight sensors, ambient light sensors, and photoplethysmographic sensors.

The portable biometric monitoring device (also referred to herein simply as "the device") has a shape and size that is adapted to be easily worn about the body of a user. It collects one or more types of physiological and/or environmental data from embedded sensors and/or external devices and communicates or relays such information to other devices or other internet-viewable sources. While the user is wearing the device, it monitors certain conditions through one or more sensors, and collects data from the sensors. For example, the device can calculate the user's step count from collected data, store the step count, then subsequently transmit user data representative of the step count to an account on a web service (such as www.fitbit.com, for example) where the user data is stored and processed, and can be viewed by the user. Indeed, the device may monitor measure or calculate many other physiological metrics in addition to, or in place of, the step count. These include, but are not limited to, energy expenditure, floors climbed or descended, heart rate, heart rate variability, heart rate recovery, location and/or heading (e.g., using global positioning system (GPS) components), elevation, ambulatory speed and/or distance traveled, swimming lap count, bicycle distance and/or speed, blood pressure, blood glucose, skin conduction, skin and/or body temperature, electromyography, electroencephalography, weight, body fat, and respiration rate. The device may also measure or calculate metrics related to the environment around the user such as barometric pressure, weather conditions, light exposure, noise exposure, and magnetic field.

The device may incorporate one or more user interface methods such as visual methods, auditory methods, or haptic methods (such as touch input or vibration). The device may display the state of one or more of the information types available and/or being tracked. For example, information can be displayed graphically, or conveyed by the intensity and/or color of one or more light emitting diodes (LEDs). The user interface may also be used to display data from other devices or internet sources. The device may also provide haptic feedback to the user through, for instance, the vibration of a motor or a change in texture or shape of the device.

The device may implement wireless communications so that when the user and device come within range of a wireless base station or access point, the stored data automatically uploads to an internet viewable source such as a website. Wireless communication may be achieved through one or a combination of methods known in the art such as Bluetooth, Bluetooth Smart, radio frequency identification (RFID), near field communication (NFC), Zigbee, Ant, optical data transmission, etc. The device may also contain wired communication capability (e.g., universal serial bus (USB)).

Methods and apparatus for pairing of the device to a server through a client, or to a server directly, are disclosed herein. In this document, the term "client" refers to client software or a client device that primarily acts as an access portal to a server. The term "server" refers to a server in communication, directly or indirectly, with one or more of the device and the client. In pairing the wireless device to a server two actions should occur. First, the account that the device is to be paired with is authenticated. Many authentication methods are currently used publicly, perhaps the most common being username and password authentication. The second action to be performed is identification or verification of the specific device for which pairing is being attempted. Embodiments of the invention relate to the second action.

FIGS. 1-4 are block diagrams of portable device systems according to various embodiments. Referring to FIG. 1, a system 100 includes a server 106, and a laptop computer 104. A non-portable computing device such as a desktop computer or health station may be used in place of computer 104. Computer 104 executes client software that recognizes and communicates with multiple portable devices 101. In this document, computer 104 and similar system elements that execute the client software are simply referred to as the client (e.g., client 104). As an example of a device embodying the apparatus described herein and participating in the processes described herein, a Fitbit™ portable monitoring device is shown as device 101. However, the apparatus and methods herein are appropriate for many other devices that perform various functions and communicate wirelessly, whether or not they are portable or have a small form factor.

A cell phone 102 is also part of system 100. As described further below, device 101 can be paired to cell phone 102 without the involvement of a server 106, in which case cell phone 102 is effectively the server. Note that a cell phone 102 may be replaced by any mobile computing device including but not limited to tablets, laptops and netbooks or any non-mobile computing devices such as desktop computers and health stations. Cell phone 102, in an embodiment, executes client software as a mobile application. Server 106 represents one or many network servers (e.g. internet servers) that store user data collected by device 101. In an embodiment, server 106 also stores and administers user account data. In an embodiment, a device user has an account that allows the user to view and operate on user data through user interfaces managed by the server 106. The user may access the user interfaces via a web site hosted and administered by server 106, and/or by using a specific mobile application on one or more client devices such as device 102.

As indicated in FIG. 1, devices 101 are paired with client devices 104 and/or 102 and these client devices are, in turn, in communication with server 106 for the purpose of transferring data from the devices 101 to server 106.

Figure 2:
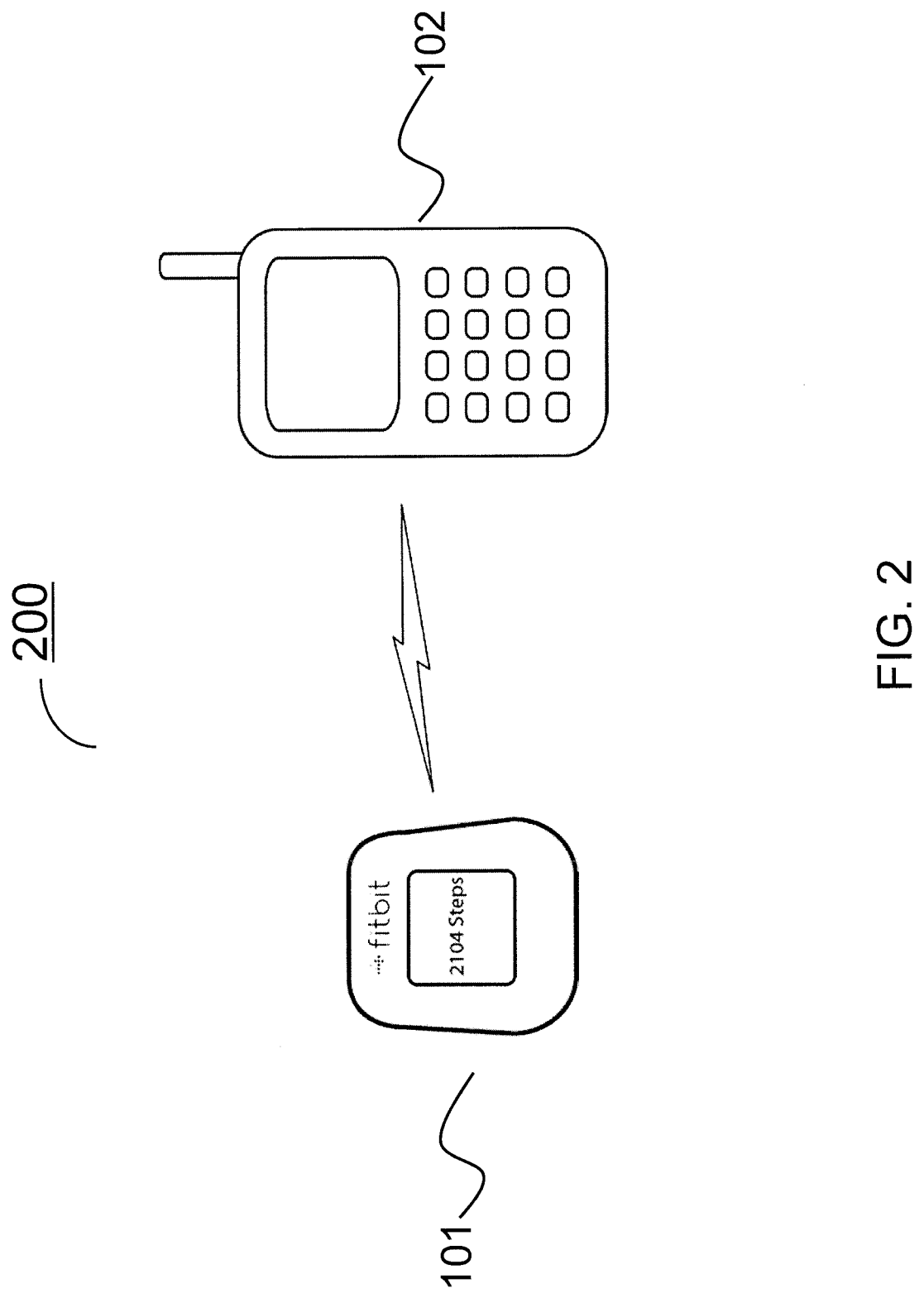
Figure 3:
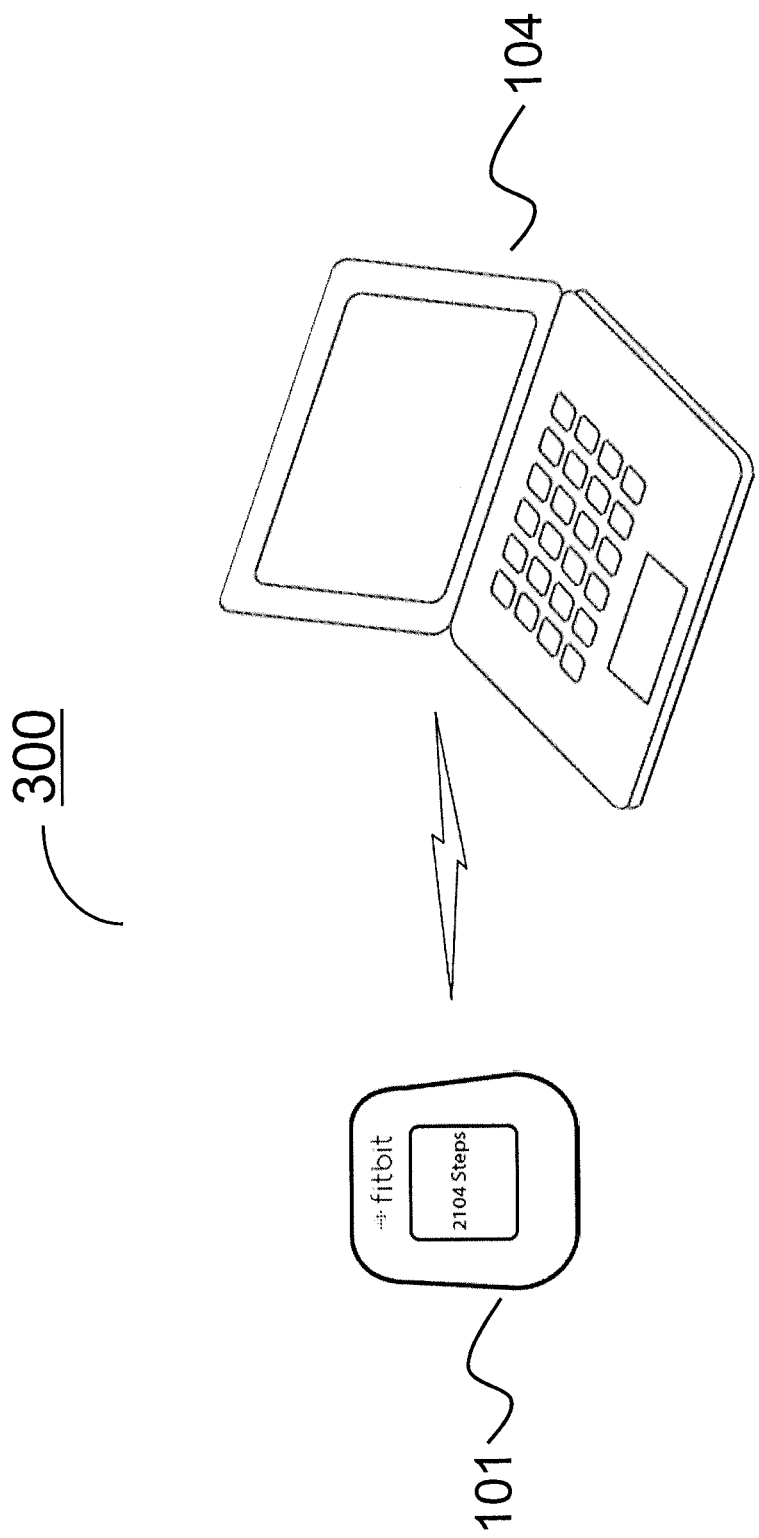

FIG. 2 is a block diagram of a system 200 including a device 101 and a mobile phone 102. In this system configuration, cell phone 102 acts as a server. This diagram also illustrates that the disclosed pairing can occur directly to a server. Similarly, FIG. 3 is a block diagram of a system 300 including a device 101 and a personal computer 104 such as a laptop, tablet, desktop computer, or health monitoring station. Personal computer 104 is also representative of any other computing devices, portable or non-portable that anyone reasonably skilled in the art could envision. In this context, computing device 104 is the server.

Figure 4:
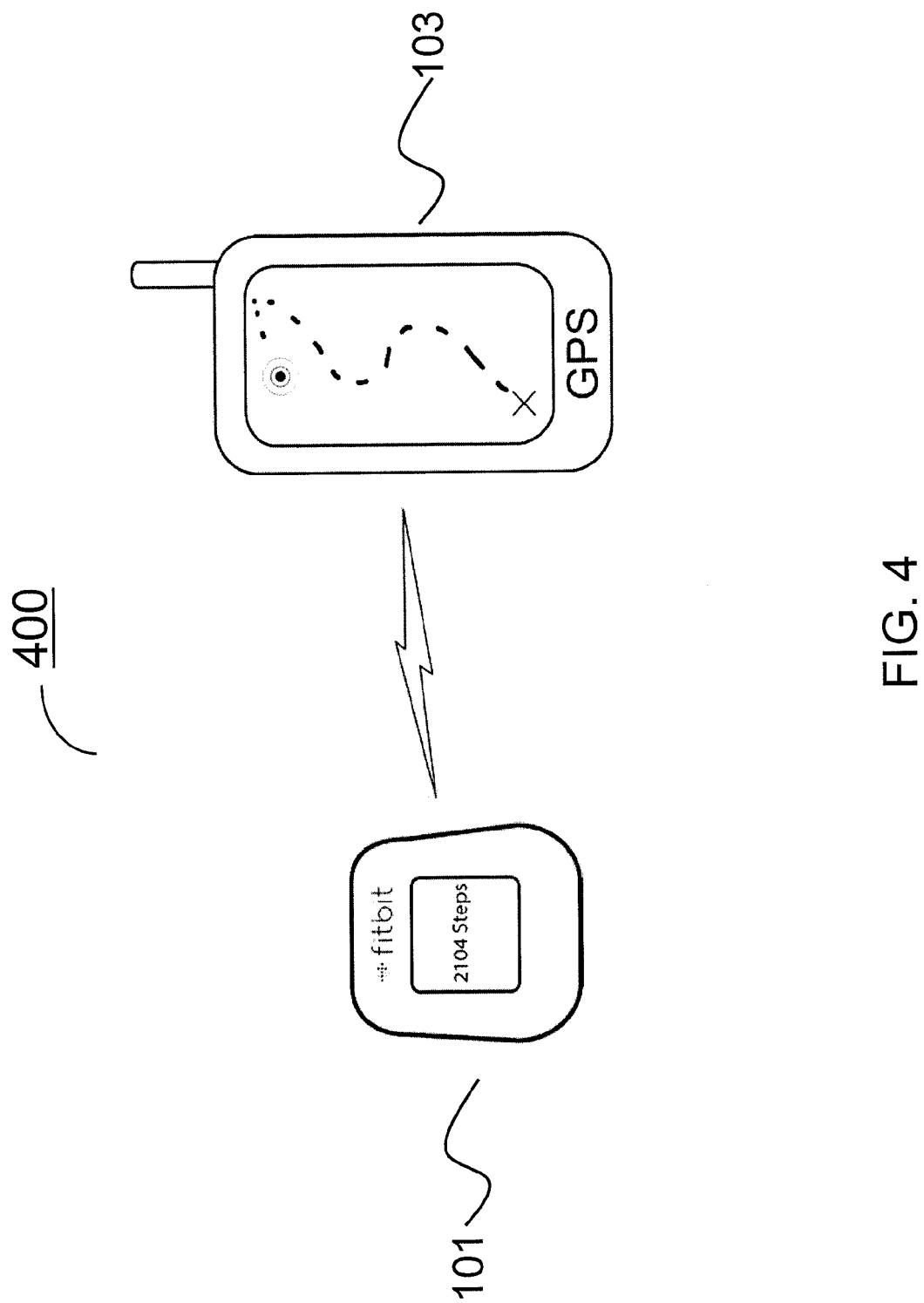

FIG. 4 is a block diagram of a system 400 including a device 101 and a second, dissimilar device 103. In various embodiments, device 103 is a portable device that communicates wirelessly and is intended to perform functions that are different from or complimentary to functions performed by device 101. As just one example, device 103 is a global positioning system (GPS) device that runs its own applications and optionally communicates with its own servers, its own web site, and its own user account. As another example, the devices 103 and 101 may not have respective "accounts" per se, but may be linked or paired to one another through the methods disclosed herein.

FIGS. 5A-5F are block diagrams of user interfaces according to various embodiments. FIG. 5A shows a user interface including a display. FIG. 5B shows a user interface including a speaker. FIG. 5C shows a user interface including a display and a speaker. FIG. 5D shows a user interface including a display and an input mechanism. The input mechanism includes (without limitation) one or more of buttons, knobs, switches, a microphone and a touch screen. FIG. 5E shows a user interface including a display, a speaker, a vibramotor and an input mechanism. FIG. 5F shows a user interface including a display, a speaker, a vibramotor, and an input mechanism. The input mechanism includes any or all of the elements from FIGS. 5D and 5E, and also includes vibration and gesture recognition sensors.

Figure 6:
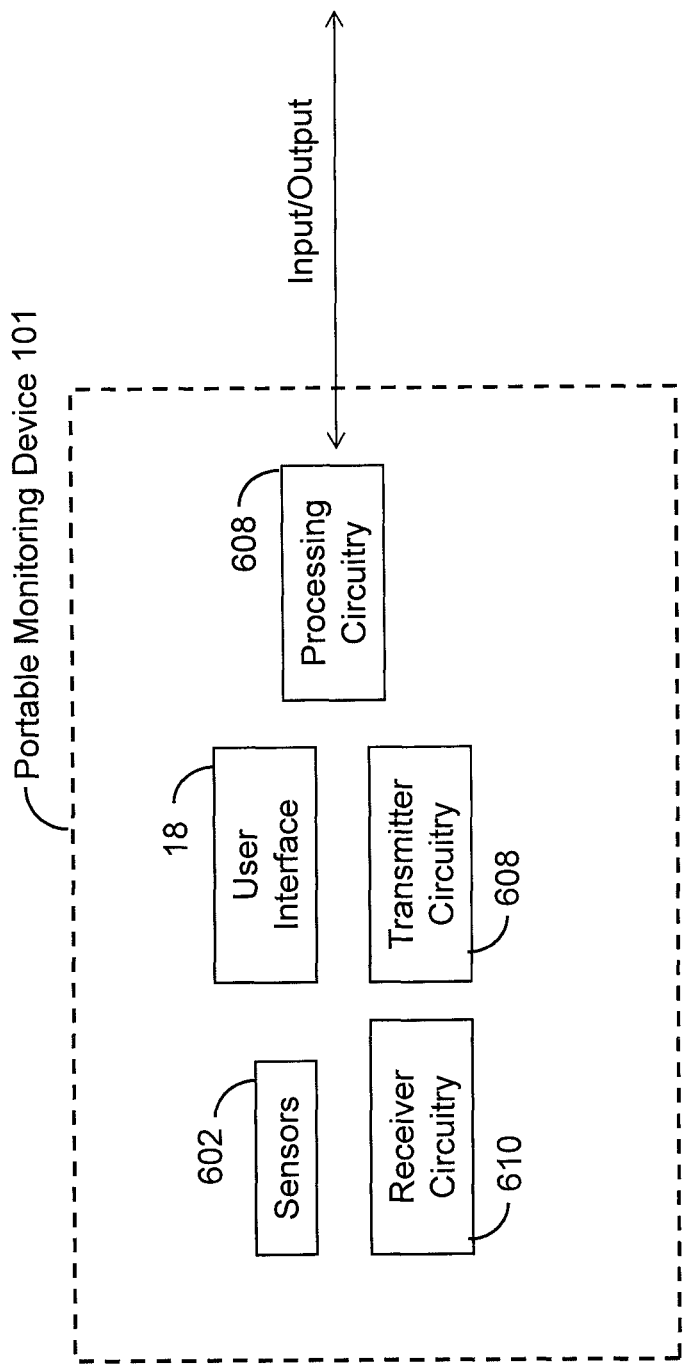
FIG. 6 is a block diagram of a portable monitoring device according to an embodiment.

FIG. 6 is a block diagram of a portable monitoring device 101 according to an embodiment. Device 101 includes the user interface 18, sensors 602, processing circuitry 604, transmitter circuitry 608, and receiver circuitry 610. The portable monitor device contains sensors 602 that are used to sense signals generated by the physical world. From these sensed signals, in one embodiment, the processing circuitry 604 calculates metrics associated with the user. These metrics may be related to sleep activity (e.g., sleep phases, sleep quality, number of awakenings, duration, time), physical activity (e.g., steps, calorie burn, weight training, running distance and/or speed, etc.), physiological parameters (e.g., heart rate, blood glucose, blood oxygenation, blood pressure, skin conductance, skin temperature, body temperature, heart rate variability, skin pigmentation, etc.), environmental parameters (e.g., humidity, temperature, UV light level, ambient noise, air quality, location, barometric pressure), and/or derived parameters (e.g., stress level, health or fitness level, disease state, sitting vs. standing vs. lying down recognition, elevation, etc.). In an embodiment, the sensors 602 include motion sensors such as an accelerometer, gyroscope, or piezoelectric film that are used individually or in combination to sense physical phenomena from which are calculate one or more of the aforementioned parameters. Sensors 602 also detect user inputs, such as a taps for example. In various embodiments, one or more a user taps is sensed by an accelerometer when the user quickly touches any part of the exterior of the device. In other embodiments, a user tap is sensed by a different type of sensor rather than an accelerometer. The device is configurable to distinguish a user tap from other forms of contact with the external world. In an embodiment, the device is "primed" or prepared to sense a user tap under certain predefined conditions, but that is not a requirement.

In another embodiment, the sensors 602 comprise motion sensors that are designated as an input mechanism to detect inputs such as a tap, but are not utilized for the tracking of other user metrics. In yet another embodiment, user interactions such as taps may be detected by a capacitive touch sensor or audio sensor.

Another pairing operation that may be of interest to a user of a wireless device is the linking of two or more portable devices to connect online social network accounts and/or perform an online social network activity or action (e.g. "like") with each of the devices. Data other than online social network identity and/or online social network activity (e.g. "likes") may also be transferred between devices including but not limited to biometric data and contact information. The portable devices need not be of the same type, or perform the same primary functions.

Client Determination of Devices Eligible for Pairing

The client may determine a subset of devices eligible for pairing before the user identifies the specific device that should be paired. This may be accomplished by determining which devices are wirelessly communicating with the client. Communicating in this context may mean one party (device, client, server, set of devices, set of clients, or set of servers) broadcasting packets and the other party listening for and receiving packets (unidirectional communication). In unidirectional communication, the party broadcasting may do this automatically without being aware of any listeners. Alternatively, the broadcasting party may be aware of the listener through a variety of methods. In certain cases, the broadcasting party may tailor its communication to a specific other party or set of other parties. Communicating may also mean that both parties are listening for and receiving packets either simultaneously or in some sequence (bidirectional communication). In an embodiment, an even smaller subset of devices is created by choosing devices that have a certain minimum signal strength (e.g. as indicated by a received signal strength indicator (RSSI) signal). In another embodiment, the client chooses a subset of a class of wireless devices that are both communicating to the client wirelessly and have high signal strength, which indicates physical proximity to the client. In this context, device class may refer to a set of device characteristics including but not limited to model, sensor type, sensor set, manufacturer, and characteristics of the account associated with the device including but not limited to account level (such as a "standard" account, or a premium account that includes more features, typically for a fee) and user gender. In other embodiments, alternative machine-readable indications of physical proximity are used independently or together to determine which devices can be paired. These indications of physical proximity may include but are not limited to NFC, RFID, GPS, Wi-Fi, Zigbee, Ant+, Bluetooth, BTLE, other radio network communication, optical detection either through machine vision, audio signals, optical data transmission, or the spectral signature of a light source on the device.

Information associated with the user's account may be used to determine which devices are eligible to be paired. This information may also be used in determining a device class. Information entered into the client, server, or a third entity in communication with either the client or server, such as a web site may also be used to determine eligibility or device class. This information includes, but is not limited to information regarding a purchased device such as model number or other model identification, color, device serial number, unique device identifier, battery level of the device, whether the device is already paired, and the type or level of the user's account (such as a "normal" account, or a premium account that includes more features, typically for a fee). Other information regarding the user may include user gender, user age, and whether the user is human or non-human (e.g. a pet).

In another embodiment, the client, account, or server to which the user would like to pair a device is compatible only with a certain device class. In such a case, the device class limitations of the client or account can be used as eligibility criteria. For example, if a user has an account associated with a corporate wellness program that only allows a specific model of device, only the allowed model is considered eligible for pairing. This is useful in a wellness program to make sure that participants in the program use devices approved by the administrators of the program. Approval of a device can be based on device model characteristics such as accuracy, precision, sampling frequency, and/or types of data which the device can track. In another example, a client is able to administer only a specific set of devices. For example, assume that an iPhone is a client that can communicate with a device, but cannot synchronize (sync) its data to a server. In such a case, the device can be determined to be ineligible for pairing.

In another embodiment, the device and/or client are capable of creating and/or detecting vibrations, for example with a vibramotor and an accelerometer. Proximity can be determined from the strength of the vibration signal from either the device to the client or the client to the device. Data can also be transferred using this method as a physical network transport layer. For example, bits could be encoded in physical vibration patterns which are detected by the accelerometer of a receiving device. In one embodiment, the device is placed on or next to a computing device running a client (such as a laptop or smartphone) in order to transfer data and/or determine device proximity. Vibration could also be transferred from device to device through physical contact of their outer cases or through an intermediary such as a tabletop or desk.

In one embodiment, the client does not proceed with pairing until the subset of devices is narrowed down to a single device as determined by best signal strength. If two or more devices are a similar distance from the client transceiver, causing them to have similar signal strengths, the client cues the user to move the device that they want to pair closer to the transceiver than the other devices. Then the client again looks for a single device with a signal strength significantly higher than any other devices, and if it find such a device, continues with the pairing process.

In another embodiment, the client proceeds with the pairing process even if there are multiple devices eligible for pairing. This is useful when there is one client attempting to pair many devices. In a case where there is more than one client attempting to pair nearby devices at the same time, the previous embodiment may prove to be a more robust pairing process.

Once the client has chosen which device or set of devices is eligible to be paired, it prompts each chosen device to indicate its eligibility to be paired. Chosen devices can indicate eligibility to be paired in one or more manners including, but not limited to vibration, illumination, sound, displayed message, or displayed symbol.

User Interacts with Device to Identify and Verify that it should be Paired

The device conveys to the user its eligibility to be paired by vibrating, lighting up, making a sound, displaying a message, or any one of multiple indications available in the art. The user chooses the device to be paired by interacting with the device once he has recognized that the device is conveying it eligibility to be paired. In one embodiment, the user causes the device to communicate its readiness to be paired (also referred to as validation) to a client or server by tapping or double tapping the device. The device senses a tap on any part of its exterior as a validation input from the user.

Other validation interactions include, but are not limited to multiple taps of the device, pressing a button, picking up the device, performing a gesture holding or wearing the device, either touching or performing a gesture on a touch sensitive part of the device, and entering some data about the device or displayed on the device into the client (e.g. entering a code displayed on the device into the client). In other embodiments, the device displays a code. The code is variously created by the device, the client, or the server, or is an algorithmic combination of codes from one or more of these sources. In one example, the server sends the device a code which is algorithmically combined with one or more codes created and/or resident on the device. This algorithmic combination is sent back to the server. The device can display one or more of these codes or algorithmic combinations of codes. In an embodiment, the client prompts the user to enter the code(s) displayed. The code that the user enters is used by the server as validation that the user wants to pair that specific device, and also that the user has the device in his possession. Codes include any types of codes as known in the art, such as random codes, pseudo-random codes, and non-random codes such as a serial numbers or other device identifiers. In various embodiments, a code can change with time, remain the same, or be unique to each session (e.g. pairing session). Use of codes as just described is just one embodiment. Use of codes in this way is not required. In other embodiments codes can be communicated without involvement of the user. For example, the device my transmit codes for the paring process by encoding device vibrations, or any other wireless or wired form of communication.

For validation, the user can interact with the device once or multiple times, or until the device gives feedback to the user acknowledging the interaction. Feedback from the device includes, but is not limited to, haptic feedback, vibration, illumination, sound, or a displayed message or symbol. In another embodiment, the lack of any of the above feedback indicates that the device has been successfully validated or identified for pairing.

In an embodiment, the device lights up once the client determines that the device is eligible to be paired. The device continues to light up until it detects the user tapping the device, at which point the device vibrates and then extinguish its lights. At this point the device is successfully identified for pairing, and the device and client communicate to complete pairing.

Figure 7:
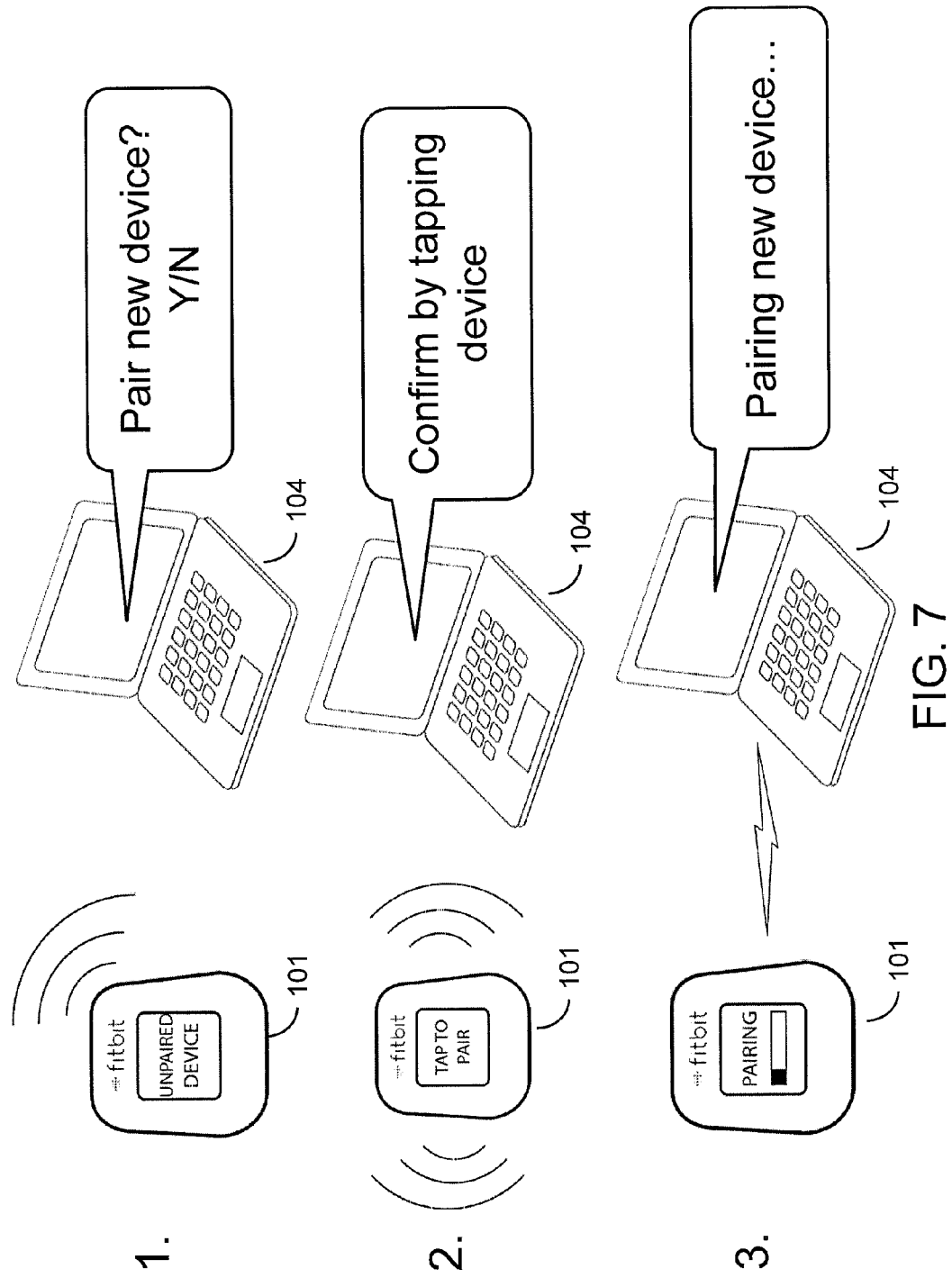
FIG. 7 is a diagram illustrating a device pairing process according to an embodiment.

FIG. 7 is a diagram illustrating a device pairing process according to an embodiment. As shown at 1, the client 104 (through a user interface) asks the user whether or not to pair the new device that has been detected. At 2, the client asks the user to confirm consent to the pairing process by tapping the device. At 3, the user taps the device, which causes the pairing operation to begin. The progress of the pairing operation may be displayed on a user interface of the device 101, and status may also be indicated by the user interface of client 104.

Figure 8:
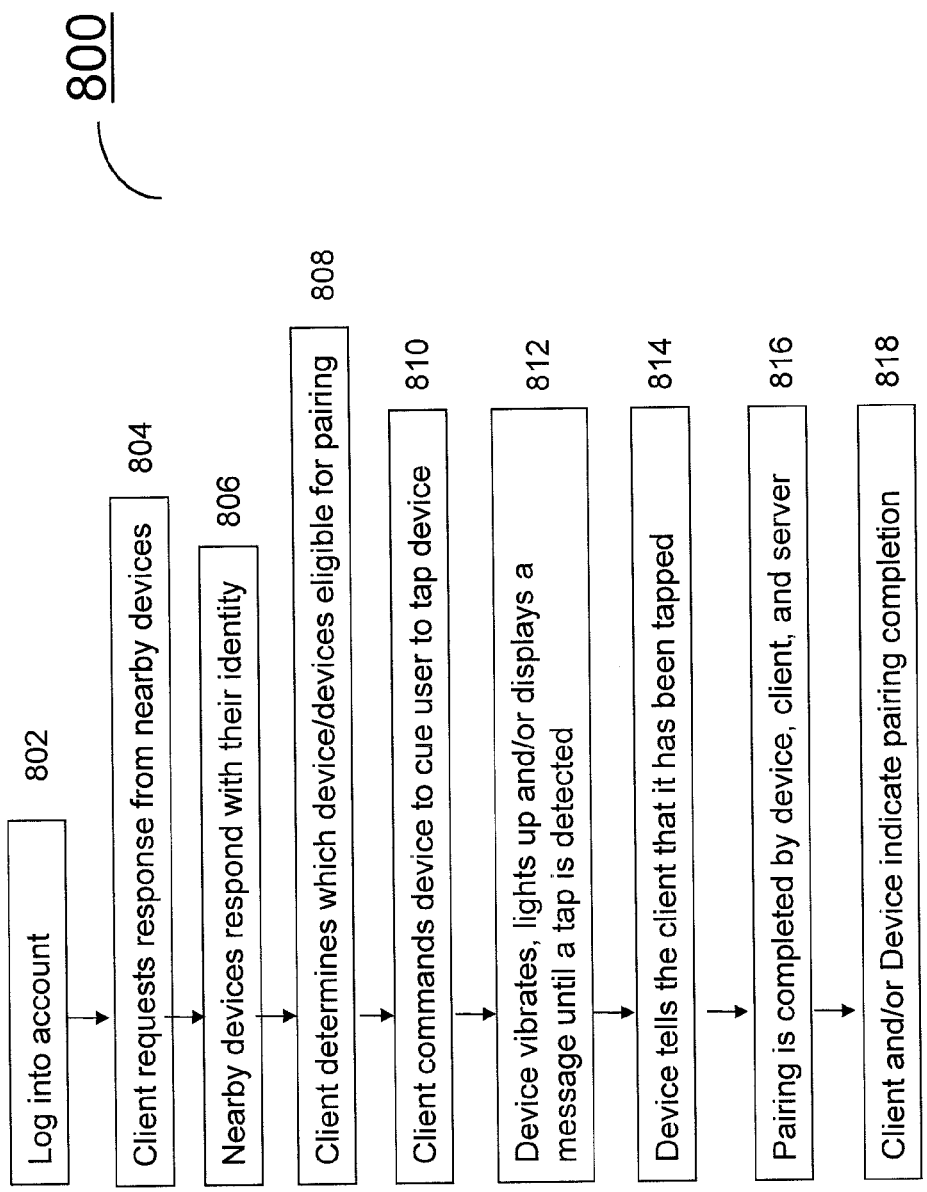
FIG. 8 is a flow diagram illustrating a process of pairing multiple devices according to an embodiment.

FIG. 8 is a flow diagram illustrating a process of pairing one or multiple devices according to an embodiment. At 802 the user logs into his or her user account. The user logs in with any client as described herein, such as a mobile phone or a computer. At 804, the client requests a response from nearby devices. In another embodiment, at 804 the client listens for any devices that are automatically broadcasting, allowing the client to determine which devices are nearby (close enough to communicate for the pairing process). Devices 101 that are nearby respond (806) automatically, including indicating their identity, for example by transmitting a device serial number, media access control (MAC) address, unique device identification (UDID), international mobile equipment identifier (IMEI), universally unique identifier (UUID), keys or any other data that can identify a unique device or unique set of devices. The client determines which devices are eligible for pairing at 808. As previously described "client" implies either a computer, mobile computing device such as a smartphone, a server, or some combination of the three. Pairing eligibility is determined by one or more criteria including but not limited to those already disclosed. The client commands identified eligible devices to cue the user to tap the device (810). The device responds to the command by communicating with the user in one or more ways, including vibrating, lighting up, and displaying a message (812). The device continues communicating to the user until the user taps the device; then the device tells the client that it has received the tap input from the user (814). The pairing process is then completed by the client, device and possibly the server (816). When the pairing process is complete, this is indicated through the user interface of one or more of the client, internet web site, and the device (818).

Figure 9:
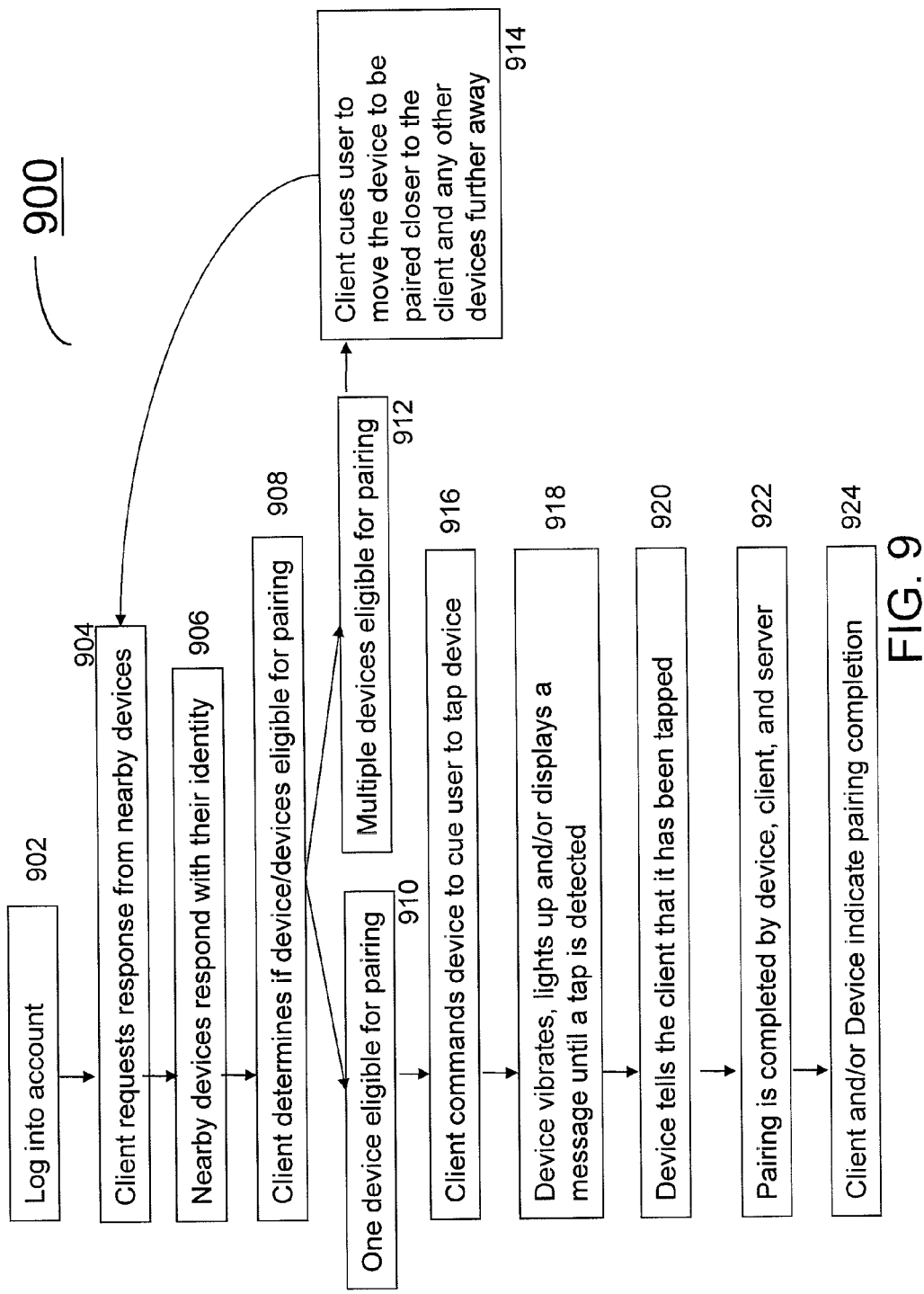
FIG. 9 is a flow diagram illustrating a process of pairing a single device according to an embodiment.

FIG. 9 is a flow diagram illustrating a process of pairing a single device according to an embodiment. At 902 the user logs into his or her user account. The user logs in with any client as described herein, such as a mobile phone or a computer. At 904, the client requests a response from nearby devices. In another embodiment, at 904 the client listens for any devices which are automatically broadcasting, allowing the client to determine which devices are nearby. Devices 101 that are nearby respond (906) automatically, including indicating their identity, for example by transmitting a device serial number, MAC address, UDID, IMEI, UUID, keys, or any other data that can identify a unique device or unique set of devices. The client determines which devices are eligible for pairing at 908. As previously described "client" implies either a computer, mobile computing device such as a smartphone or a server, or some combination of the three. Pairing eligibility is determined by one or more criteria including but not limited to those already disclosed.

In some situations a single device is eligible for pairing (910), and in other situations multiple devices are eligible for pairing (912). When there is one device eligible for pairing, the client commands the eligible device to cue the user to tap the device (916). The device responds to the command by communicating with the user in one or more ways, including vibrating, lighting up, and displaying a message (918). The device continues communicating to the user until the user taps the device; then the device tells the client that it has received the tap input from the user (920). The pairing process is then completed by the client, device and possibly the server (922). When the pairing process is complete, this is indicated through the user interface of one or more of the client, internet website, and device (924).

In one embodiment, when there is more than one device eligible for pairing (912), the client cues the user (through the user interface as previously described) to move the device to be paired closer to the client, and to move other devices away from the client (914). The process then returns to 904, where the client requests a response from nearby devices.

Figure 10:
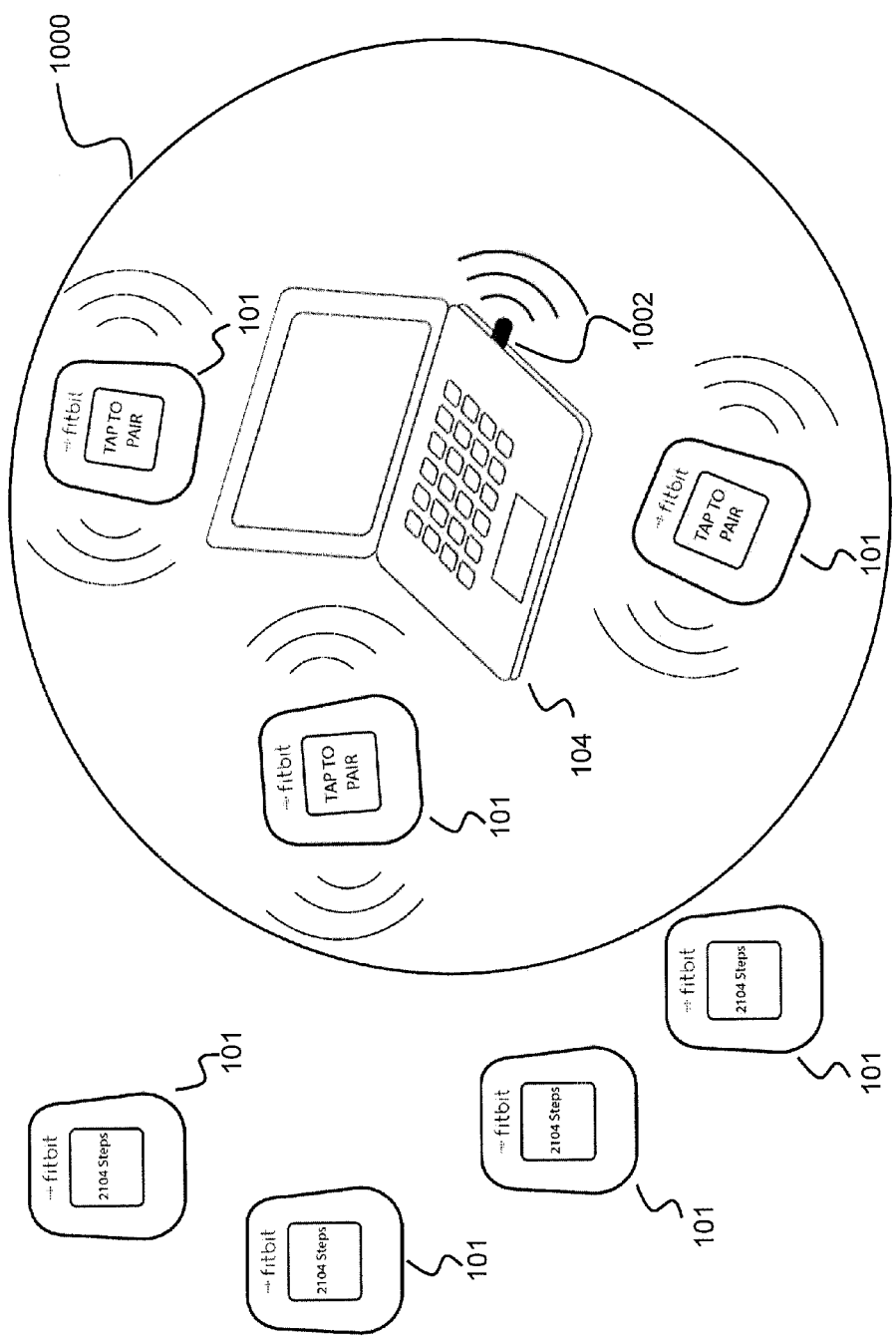
FIG. 10 is a block diagram of a configuration of a client and multiple devices according to an embodiment.

FIG. 10 is a block diagram of a configuration of a client and multiple devices according to an embodiment. FIG. 10 shows area 1000 inside of which devices 101 are nearby devices that are detectable by client 104 using a wireless communication dongle 1002. Other devices 101 are shown outside of area 1000. The devices 101 inside area 1000, in one embodiment, are vibrating to indicate to the user that pairing is being requested. FIG. 10 corresponds to a method of pairing described in FIG. 8.

Figure 11:
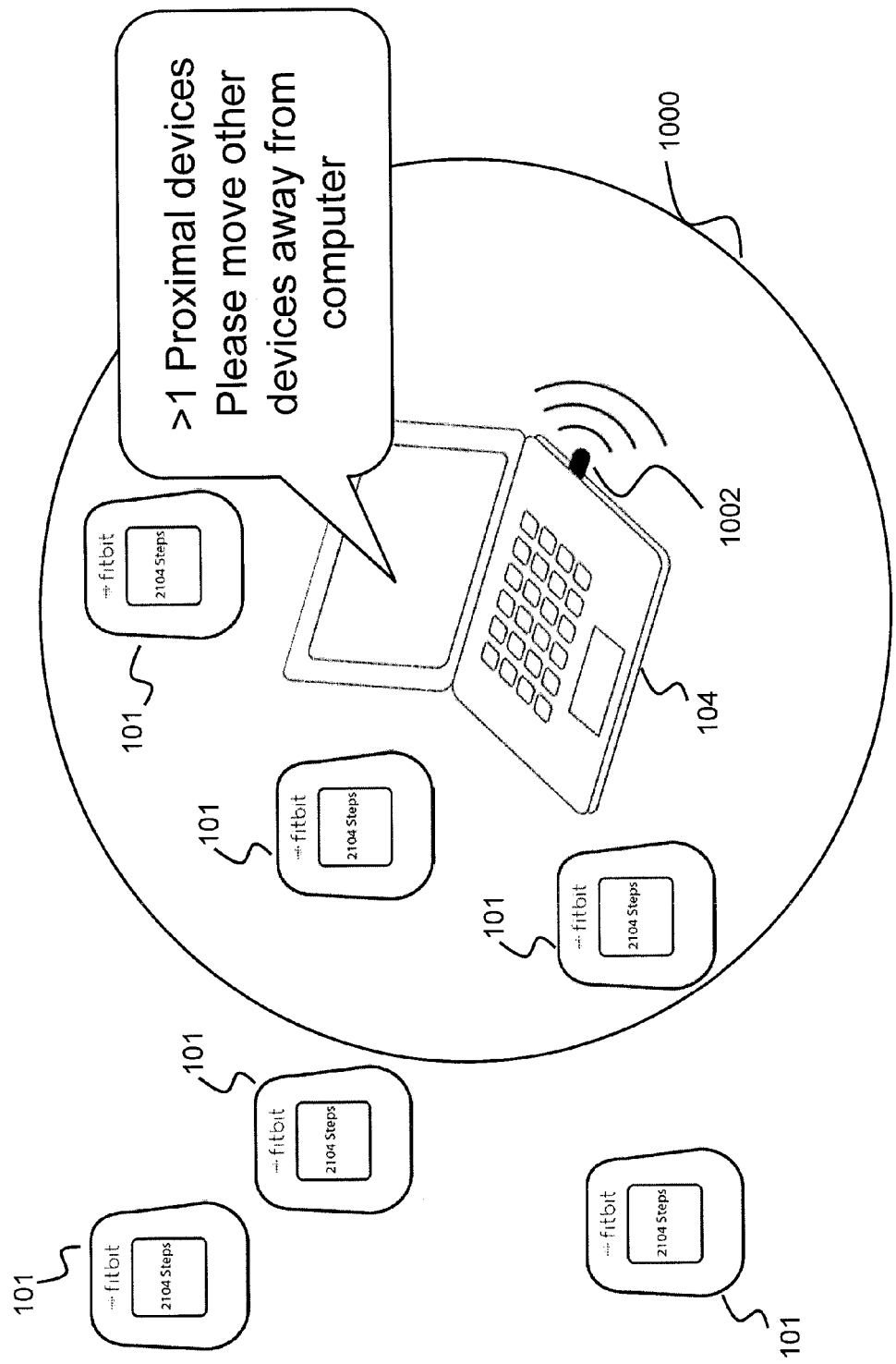
FIG. 11 is a block diagram of a configuration of a client and multiple devices according to an embodiment.

FIG. 11 is a block diagram of a configuration of a client and multiple devices according to an embodiment. This diagram illustrates a process in which the client 104 asks the user of devices 101 to move outside of area 1000 those devices that are not to be paired at this time. FIG. 11 corresponds to a method of pairing described in FIG. 9.

Figure 12:
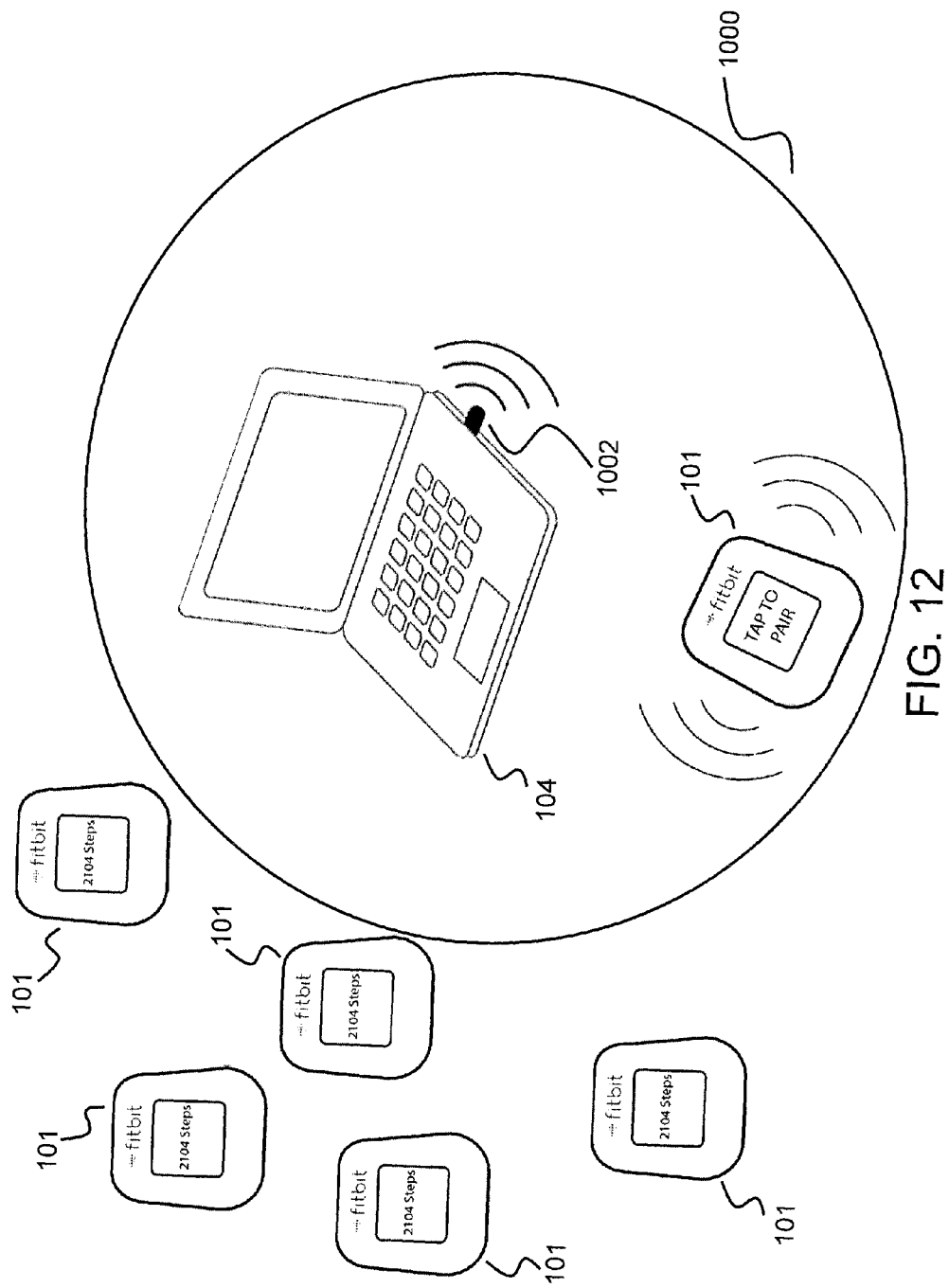
FIG. 12 is a block diagram of a configuration of a client and multiple devices according to an embodiment.

FIG. 12 is a block diagram of a configuration of a client and multiple devices according to an embodiment. In this diagram, the user has moved all of the devices 101 outside area 1000 except the single device 101 to be paired.

Figure 13:
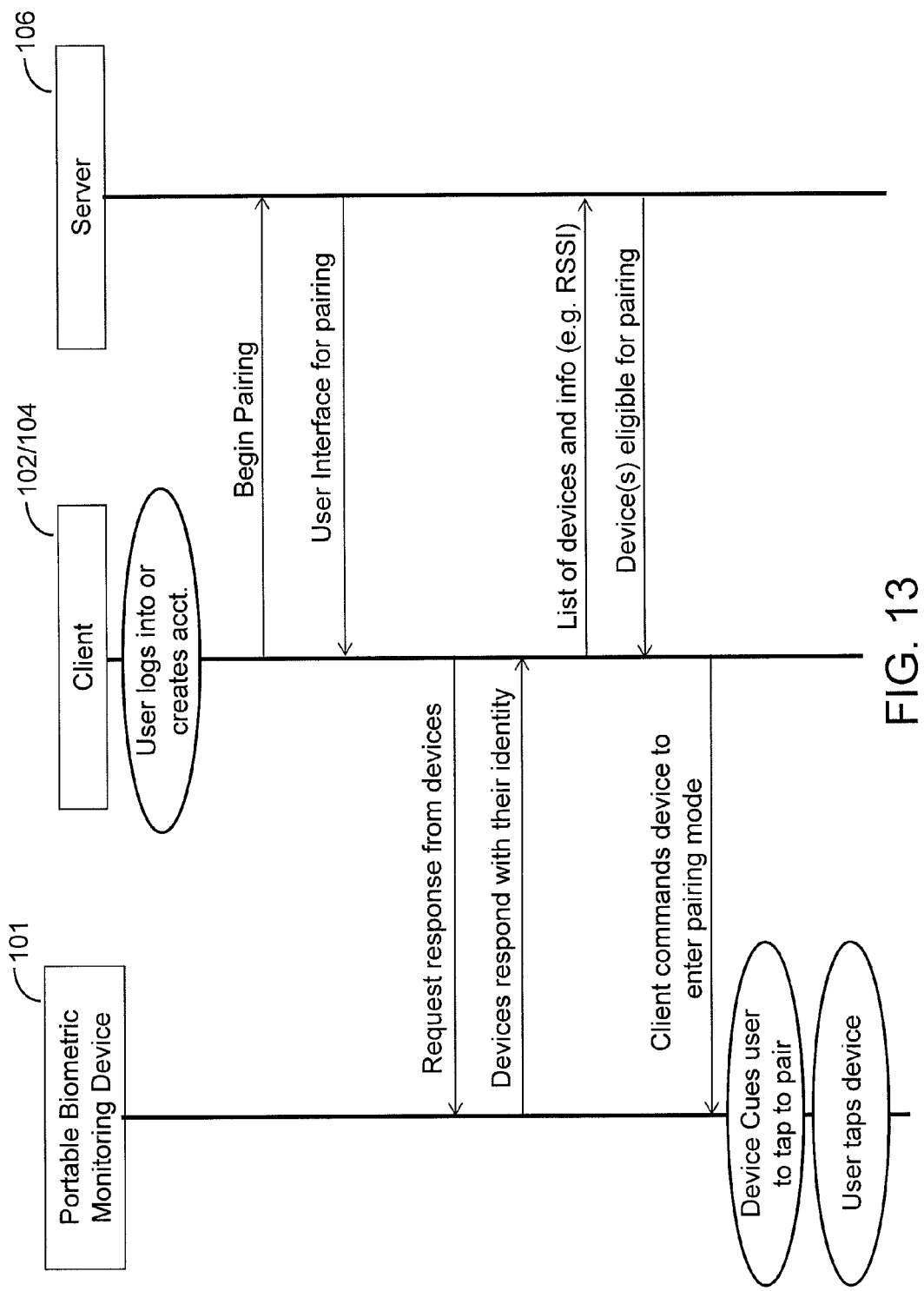
FIG. 13 is a signal diagram for a pairing operation according to an embodiment.

FIG. 13 is a signal diagram of one embodiment of a pairing communication involving a device 101, a client 102 (or 104) and a server 106. Reading the diagram from the top, when a user logs into his or her user account, or creates a user account, the client tells the server to begin a pairing process. The server provides the user interface for pairing or tells the client to display the user interface for pairing. The client requests responses from nearby devices. In an embodiment, the request is a broadcast signal expected to be recognized by the intended devices. Intended devices within range respond to the client with their respective identity information. The client relays the device identity information to the server. When more than one device responds, the relayed information includes a list of devices. The relayed information also includes all of the information received for each device, which can include RSSI, unique identifiers, etc. From this relayed information the server determines which devices are eligible for pairing. An identification of the eligible devices is sent to the client. This identification can be one or more items of information, including but not limited to a unique identifier, and the corresponding RSSI. To each of the eligible devices, the client sends a command to enter pairing mode. The receiving devices enter pairing mode, including cuing the user to consent to pairing, as described herein. In an embodiment, the user taps the device to consent to, and initiate, pairing. In an embodiment, the cue to the user is device vibration, but any other cue can be used, such as illumination of the device, a sound, etc.

Figure 14:
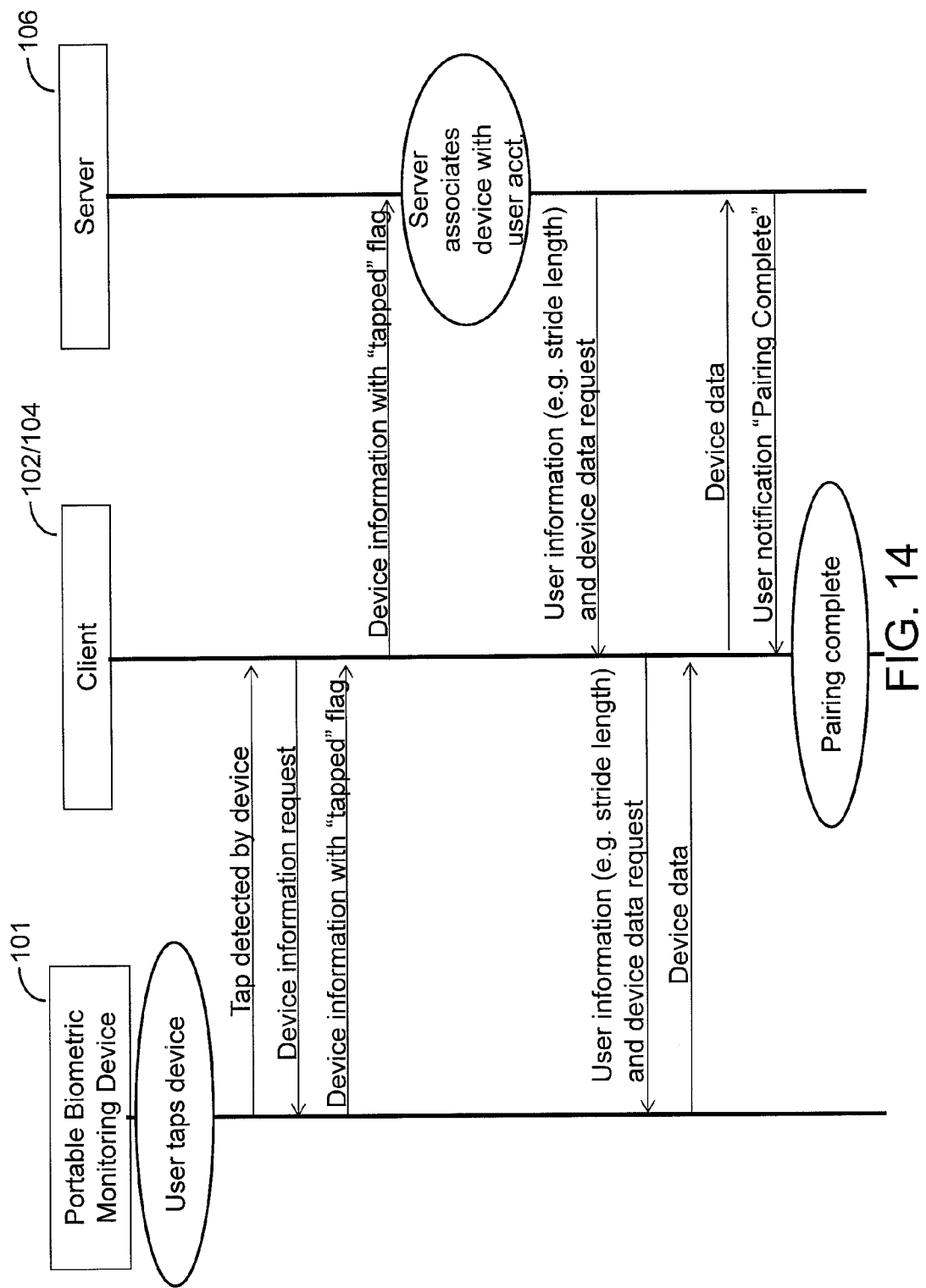
FIG. 14 is a continuation of the signal diagram of FIG. 13.

FIG. 14 is a signal diagram continuing to illustrate the pairing communication involving the device 101, the client 102 (or 104) and the server 106. The user tap is detected by device sensor, causing the device to signal the client, and the client returns a device information request to the device. The device responds by sending the client the requested device information as well as a "tapped" flag. This device information and the flag are transmitted to the server by the client. The server uses the device information to associate the device with a user account. The server then accesses user information (as previously calculated or entered by the user into the account). The user information can include any of the items previously described, such as height, weight, stride length, etc. The server sends the user information to the client along with a device data request. The server forwards the user information and device data request to the device. The device responds with device data, which is forwarded from the client to the server. The server now has the data required to complete the pairing process. When the process is complete, the server sends a "pairing complete" notification to the client. FIGS. 13 and 14 are representative of but one example set of communications. As previously discussed, there can be many variations within the scope of the invention as claimed, including a direct device-server communication, omitting the client, and various methods of notifying the user and of receiving user input. In scenarios in which a cell phone (for example, as in FIG. 2) acts as the server, data from the device-cell phone communication can be uploaded at a later time to yet another, remote server.

Client/Device Pairing Initialization and Completion

To complete pairing in an embodiment, the validated device sends a special code to the client and/or server indicating that the user verified their desire to pair that specific device. Final pairing steps then proceed between the device, client and/or server. In an embodiment, these steps include the transfer of user data from the client or server to the device. User data includes, but is not limited to, gender, height, stride length, weight, body mass index (BMI), basal metabolic rate (BMR), goal data (e.g. a daily step or calorie goal), server account information (e.g., information from an online account through which the user can view and manipulate data recorded by their device), age, location, and historical user data such as the number of calories burned in the last month, week, or day. In an embodiment, the user enters various user data when setting up or modifying his or her account through a user interface on a client device. These pairing steps may also include the transfer of device data to the client and/or server such as device serial number, model, media access control (MAC) address, time of manufacture, manufacturing batch, and any calibration data.

The completion of pairing can be indicated on the client and/or the device in a variety of manners. For example, the device can vibrate, light up, play a sound, display a message, or display a symbol. A laptop or PC client can also indicate completion of paring in one or more of the foregoing manners. Successful pairing can also be indicated on a user account hosted by the server and accessible through a web browser or internet-connected application on a PC or mobile computing device such as a smartphone or tablet.

Peer to Peer Device Pairing

Two or more devices may be paired without the use of a client. This is referred to herein as "linking". In one embodiment, the user interacts with the device to turn on a linking mode. In the linking mode, the initiator device sends out a signal to devices within wireless communication range requesting to link with them. Receiving devices may indicate that they are ready to be linked in one or a combination of the following manners: vibration, illumination, sound, displayed message, or displayed symbol. The user or users then indicate that they perceive the indication by performing a validation interaction such as the ones listed above (e.g., tapping the device anywhere on its surface). Once validated, the devices communicate with the initiator device to exchange data.

In another embodiment, the linking is performed without the user having to set one or more devices to a linking mode. In such a case, the users perform one or more gestures associated with linking. In one embodiment, two users may tap their two devices together. After tapping them, the devices may ask the user to confirm the linking through an indication such as the ones listed above. The user confirms the linking by performing a second interaction with the device such as those listed above, for example by tapping the devices again.

Instead of tapping the two devices together as in the first part of the previously described process, an NFC tag, RFID tag or other wireless communication protocol may be used. In such an embodiment, two or more users move their devices within a close enough proximity for one or more of the devices to detect one or more of the other device's passive or active NFC tags. The devices then communicate over NFC, an alternative wireless communication method, or a combination of any available wireless communication methods. To verify that the users would like to complete the linking process, the devices cue the users to tap or interact with their devices through any of the described methods including but not limited to tapping the device, pressing a button, performing a gesture on a touch screen, touching a capacitive touch sensor, or performing a gesture with the device. Once the user validates the linking, the devices complete any communication necessary to finalize the linking.

In one embodiment, this clientless device-to-device linking process allows two users to activate an online social network connection. The two devices are linked as described above so as to exchange social network credentials and/or perform an online social network action or activity (e.g. "like"). After linking, the next time either one of the devices is connected to the internet, the device signals the user's account to create a social link to the user of the linked device or perform a social network action or activity (e.g. "like"). The user of the linked device is associated with the social network credentials received from linked device.

Automatic Pairing Initiation for Unpaired Devices

In another embodiment, the portable biometric monitoring device is placed in close proximity to a computer, which causes an application to be launched on the computer. The term computer, in this context, is used to describe any electronic computing device such as a mobile phone, tablet computer, PC, desktop computer, or other biometric monitoring device (e.g., a smart weight scale). Close proximity may be detected through a number of technologies such as NFC, Bluetooth (e.g., by signal strength), or the magnetic signature of the device as detected by a magnetometer in the computer. If the device is determined to be in an unpaired state, the application initiates the pairing process including wirelessly signaling the device. Wirelessly signaling the device places the device in a pairing mode and this is conveyed to the user through, for instance, a change in the visual display of the device and/or vibrating a motor within the device. The user can then complete the linking process by tapping the device (as previously described). The device can be paired to the computer itself or to an online service (e.g., an account on www.fitbit.com). Determination of the unpaired state of the device can be done by the device knowing its state (e.g., the device knows that it is in factory state) or by the application querying a database of known devices (e.g., by discovering and looking up the serial number of the device).

Pairing with Minimal Interaction or No Interaction

In another embodiment, the client automatically pairs a device if the device and the user meet a certain requirement or set of requirements. These requirements may include, but are not limited to the device having never been paired before, the user having never paired a device before, the device being in the proximity of the client as determined by any variety of methods discussed in this disclosure, and the user's account having been created within a defined time frame. In one embodiment, when a user brings a single unpaired or new device within range of a client associated with a user account that does not already have a device paired to it, the device will automatically be paired to the account. In another embodiment, if a user brings a single unpaired or new device within range of a client associated with a user account which does not already have a device paired to it, the client will ask the user if they want to pair the device. If the user agrees to pair the device, the rest of the pairing process completes automatically without further interaction from the user.

In another embodiment, the user is not required to have an account to automatically pair a device. In one such case, the only requirement for automatic pairing is that the device is unpaired or new. Suppose the user has purchased a new, unpaired device. The client asks the user for some information that will later be used to create an account, then proceeds to pair the device, and then creates the account afterwards. This demonstrates that the user need not have an account for pairing to occur. An account can be associated with a device that is already paired, or with a device that is not yet paired. In other embodiments, there is no account per se associated with the device or user.

Automatic Account Customization

It may be desirable to automatically customize the account associated with a device before, during, or immediately after pairing. In one embodiment, a specific set of devices are registered with an account administrator, such as a server, to automatically enable, disable, or modify account characteristics. For example, a set of devices to be distributed or sold to participants in a corporate wellness program is registered with the account server before the devices are paired. The devices can be registered using unique device identifiers such as serial numbers. In an embodiment, when the eventual users of these pre-registered devices log into the appropriate web site or create an account linked to the device, the account server can automatically enroll them in a corporate wellness program. In another example, devices to be sold or distributed within a country or geographic area associated with a single language can be pre-registered with the account server. When a user creates an account, or links an account to one of these pre-registered devices, the user's account defaults to the language associated with the user's country or geographic area.

In another embodiment, the device is programmed to notify the pairing client or server to modify account characteristics before, during or after pairing. For example, all devices to be distributed to participants in a corporate wellness program group are preprogrammed to command the pairing client to enroll the account associated with the device to the corporate wellness program.

In another embodiment, the client or server modifies account characteristics based on device characteristics acquired before, during, or after pairing. For example, the layout and/or content of a user's account may automatically change depending on the device model associated with it. A device model that tracks steps and distance, but not floors may cause the user's account to display only steps and distance tracked, even though other device models may be able to track floors. The user's account may also display advertisements or notifications for devices that have different or additional features depending on the device model paired to the account.

In another embodiment, the client or server modifies account characteristics based on user characteristics acquired before, during, or after pairing. For example, if a user enters information about themselves during the pairing process such as gender, the user's account displays a specific appearance associated with the gender. Other information a user can enter about themselves includes, but is not limited to height, weight, age, date of birth, and location. Aspects of the systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the system include: microcontrollers with memory (such as electronically erasable programmable read only memory (EEPROM)), embedded microprocessors, firmware, software, etc. Furthermore, aspects of the system may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that the various functions or processes disclosed herein may be described as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the internet and/or other computer networks via one or more data transfer protocols (e.g., HTTP, FTP, SMTP, etc.). When received within a computer system via one or more computer-readable media, such data and/or instruction-based expressions of components and/or processes under the system described may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the systems and methods is not intended to be exhaustive or to limit the systems and methods to the precise forms disclosed. While specific embodiments of, and examples for, the systems components and methods are described herein for illustrative purposes, various equivalent modifications are possible within the scope of the systems, components and methods, as those skilled in the relevant art will recognize. The teachings of the systems and methods provided herein can be applied to other processing systems and methods, not only for the systems and methods described above.

The elements and acts of the various embodiments described above can be combined to provide further embodiments. These and other changes can be made to the systems and methods in light of the above detailed description.

In general, in the following claims, the terms used should not be construed to limit the systems and methods to the specific embodiments disclosed in the specification and the claims, but should be construed to include all processing systems that operate under the claims. Accordingly, the systems and methods are not limited by the disclosure, but instead the scope of the systems and methods is to be determined entirely by the claims.

While certain aspects of the systems and methods are presented below in certain claim forms, the inventors contemplate the various aspects of the systems and methods in any number of claim forms. For example, while only one aspect of the systems and methods may be recited as embodied in machine-readable medium, other aspects may likewise be embodied in machine-readable medium. Accordingly, the inventors reserve the right to add additional claims after filing the application to pursue such additional claim forms for other aspects of the systems and methods.

What is claimed is:

1. A portable monitoring system, comprising:
a first device configurable to communicate wirelessly with a second device, wherein at least one of the first device and the second device comprises a portable monitoring device comprising,
wireless transmitter circuitry;
wireless receiver circuitry;
a plurality of sensors configurable to sense a plurality of physical phenomena;
user interface means for communicating to a user, wherein the user interface means comprises one or more of a screen, a touch screen, a vibramotor, a keyboard, light emitting diodes (LEDs), and buttons; and
processing circuitry configurable to interpret data from the plurality of sensors; and wherein to communicate wirelessly includes a pairing process comprising,
the first device automatically discovering the second device by wireless communication;
the first device receiving user login information to log the user into a user account;
the first device sending a signal to a server that indicates the start of the pairing process;
the server sending user interface data for pairing to the first device;
the first device wirelessly detecting the second device, and requesting a response from the second device;
the first device receiving a response from the second device, including a device identification;
in response to the first device forwarding the received response to the server, the server sending a list of detected devices eligible for pairing to the first device;
when the second device is on the list of detected devices, the first device sending a command to the second device to enter pairing mode;
the second device cueing the user via the user interface to validate a request to pair;
the second device receiving input from the user to respond to the request, wherein the input is received by one or more of the plurality of sensors, wherein input comprises tapping only the second device anywhere on its exterior;
the second device detecting the tapping using a motion sensor; and
the first device and the second device completing the pairing process while remaining remote from each other.

2. The system of claim 1, wherein the plurality of sensor comprises a motion sensor comprising at least one of an accelerometer, a gyroscope sensor, a microphone, an altimeter, and a magnetometer, and wherein the user response to the cue is detectable by the motion sensor.

3. The system of claim 1, further comprising a client device configurable to communicate with the portable monitoring device on behalf of the server, and to communicate data from the portable monitoring device to the server.

4. The system of claim 3, wherein the client device comprises a client software application.

5. The system of claim 3, wherein the server device comprises a mobile phone.

6. The system of claim 1, wherein pairing comprises pairing the portable monitoring device with a web based user account accessible through a web site as part of a setup process, wherein user data, including data entered by the user using the web site, is downloaded to the portable monitoring device.

7. The system of claim 2, wherein the processing circuitry is further configurable to process data from the plurality of sensors to generate a plurality of biometric data based on user physical activity, and wherein after pairing, the biometric data is automatically uploaded to the server when the device is in wireless communication range with one or more of the server and a client acting on behalf of the server.

8. The system of claim 1, wherein the plurality of sensors comprises at least one of an audio sensor, an accelerometer, altimeter, photoplethysmograph, magnetometer, Global Positioning System sensor, thermometer, and a gyroscope.

9. The system of claim 8, wherein the processor operates on data from the plurality of sensors to generate one or more of number of steps taken, amount of elevation gained, and distance traversed.

10. The system of claim 8, wherein cueing comprises causing the device to perform at least one of vibrating, illuminating, making a sound, and displaying a message.

11. The system of claim 3, wherein the server is further configurable to discover multiple portable monitoring devices in proximity for pairing, and to communicate with the user through a client user interface asking that the user choose one of the multiple devices to be paired.

12. The system of claim 11, wherein asking the user further comprises asking the user to move the chosen device closer to the client and move the other devices farther away from the client.

13. The system of claim 1, wherein receiving input from the user to respond to the request comprises an accelerometer sensing the user tapping the second device anywhere on its exterior surface without the user entering any data.

* * * * *